United States Patent
Kent et al.

(10) Patent No.: US 7,276,242 B1
(45) Date of Patent: Oct. 2, 2007

(54) VIPOX VECTOR CODING AN HIV ANTIGEN AND A CYTOKINE

(75) Inventors: Stephen Kent, Camberwell (AU); Ian Allister Ramshaw, Duffy (AU); David Bernard Boyle, Leopold (AU)

(73) Assignee: Virax Immunotherapeutics Pty Ltd., Victoria (AU)

( * ) Notice: Subject to any disclaimer, the term of this patent is extended or adjusted under 35 U.S.C. 154(b) by 0 days.

(21) Appl. No.: 09/831,307

(22) PCT Filed: Nov. 9, 1999

(86) PCT No.: PCT/AU99/00989

§ 371 (c)(1),
(2), (4) Date: Jan. 7, 2002

(87) PCT Pub. No.: WO00/28003

PCT Pub. Date: May 18, 2000

(30) Foreign Application Priority Data

Nov. 9, 1998 (AU) .................................. PP7007

(51) Int. Cl.
A61K 39/12 (2006.01)
(52) U.S. Cl. ............................. 424/199.1; 424/188.1; 424/208.1; 424/232.1
(58) Field of Classification Search ............. 424/188.1, 424/208.1, 199.1, 232.1, 278.1, 85.4; 435/320.1, 435/172.3, 236

See application file for complete search history.

(56) References Cited

U.S. PATENT DOCUMENTS 5,766,598 A * 6/1998 Paoletti et al. ........... 424/199.1
5,866,136 A * 2/1999 Ramshaw et al. ....... 424/199.1

OTHER PUBLICATIONS

Haynes, B. F., et al., 1996, "Update on the Issues of HIV Vaccine Development", Ann. Med. 28:39-41.*
Lee, T.-H., 1997, "Acquired Immunodeficiency Disease Vaccines: Design and Development", in *AIDS: Biology, Diagnosis, Treatment, and Prevention, fourth edition*, DeVita, V. T., et al., eds.,Lippincott-Raven Publishers, Philadelphia, pp. 605-616.*
Letvin, N. L., 1998, "Progress in the Development of an HIV-1 Vaccine", Science 280:1875-1880.*
Burton, D. R., and J. P. Moore, 1998, "Why do we not have an HIV vaccine and how can we make one?", Nature Med. Vaccine Suppl. 4(5):495-498.*
Johnston, M.I., 2000, "The Role of Nonhuman Primate Models in AIDS Vaccine Development", Mol. Med. Today 6:267-270.*
Feinberg, M. B., and J. P. Moore, 2002, "AIDS Vaccine Models: Challenging Challenge Viruses", Nature Med. 8(3):207-210.*
Fatkenheuer, G., Thiesen, A., Rockstroh J., et al., "Virological Treatment Failure of Protease Inhibitor Therapy in an Unselected Cohort of HIV-Infected Patients", *Aids* (11):F-113-116 (1997).

Finzi, D., Hermankova, M., Pierson, T., et al., "Identification of a Reservoir for HIV-1 in Patients on Highly Active Antiretroviral Therapy", *Science* 278:1295-1300 (1997).
Ogg, G.S., Jin, X., Bonhoeffer, S., et al., "Quantitation of HIV-1 Specific Cytotoxic T Lymphocytes and Plasma Load of Viral RNA", *Science* 279:2103-2105 (1998).
Tsoukas, C.M., Raboud, J., Bernard, N.F., et al., "Active Immunization of Patients with HIV Infection: A Study of the Effect of VaxSyn, a Recombinant HIV Envelope Subunit Vaccine, on Progression of Immunodeficiency", *AIDS Res Hum Restroviruses* 14:483-490 (1998).
Eron, J.J. Jr., Ashby, M.A., Giordano, M.F., et al., "Randomised Trial of MNrgp120 HIV-1 Vaccine in Sympomless HIV-1 Infection", *Lancet* 348:1547-1551 (1996).
Veenstra, J., Williams, I.G., Colebunders, R., et al., "Immunization with Recombinant p. 17/p. 24:Ty Virus-like Particles in Human Immunodeficiency Virus-Infected Persons", *J Infect Dis* 174:862-866 (1996).
Rosenberg, E.S., Billingsley, J.M., Caliendo, A.M., et al., "Vigorous HIV-1 Specific $CD4^+T$ Cell Responses Associated with Control of Viremia", *Science* 278:1447-1450 (1997).
Agy, M.B., Frumkin, L.R., Corey, L., et al., "Infection of *Macaca nemestrina* by Human Immunodeficiency Virus Type -1", *Science* 257:103-106 (1992).
Kent, S. J., Woodward, A., Zhao, A. "Human Immunodeficiency Virus Type 1 (HIV-1) Specific T Cell Responses Correlate with Control of Acute HIV-1 Infection in Macaques", *J Infect Dis* 176:1188-1197 (1997).
Kent, S.J., Zhao, A., Best, S., Chandler, J.D., Boyle, D.B., Ramshaw I.A., "Enhanced T-Cell Immunogenicity and Protective Efficacy of a Human Immunodeficiency Virus Type 1 Vaccine Regimen Consisting of Consecutive Priming with DNA and Boosting with Recombinant Fowlpox Virus", *J Virol* 72:10180-10188 (1998).
Cardinal, B., Kent, S.J., Lab, "Behavioral Effects of Simple Manipulable Environmental Enrichment on Pair-housed Juvenile Macaques", *Primate Newsletter* (1997).
Andrew, M.E., Boyle, D.B., Coupar, B.E., Whitfield, P.L., Both, G.W., Bellamy, A.R., "Vaccina Virus Recombinants Expressing the SA11 Rotavirus VP7 Glycoprotein Gene Induce Serotype-Specific Neutralizing Antibodies", *J Virol* 61:1054-1060 (1987).
Gray, P., Leung, D., Pennica, D., et al., "Expression of Human Immune Interferon cDNA in *E. coli* and Monkey Cells", *Nature* 295:503-508 (1982).
Heine, H.G., Boyle, D.B., "Infectious Bursal Disease Virus Structural Protein VP 2 Expressed by a Fowlpox Virus Recombinant Confers Protection Against Disease in Chickens", *Arch Virol* 131:277-292 (1993).
Boyle, D.B., Coupar, B.E., "A Dominant Selectable Marker for the Construction of Recombinant Poxviruses", *Gene* 65:123-128 (1988).
De St. Groth, F., "The Evaluation of Limiting Dilution Assays", *J Immunol Methods* 49:R11-23 (1982).

* cited by examiner

Primary Examiner—Jeffrey S. Parkin
(74) Attorney, Agent, or Firm—Morrison & Foerster LLP (57) ABSTRACT

The invention relates to a fowl pox virus encoding an HIV antigen (gag and/or pol) and a cytokine (γ-interferon).

4 Claims, 7 Drawing Sheets

VIPOX VECTOR CODING AN HIV ANTIGEN AND A CYTOKINE

This application is a U.S. National Phase Application under 35 U.S.C. 371 of PCT Application Ser. No. PCT/AU99/00989, filed Nov. 9, 1999, which claims priority to AU Application No. PP7007, filed Nov. 9, 1998.

FIELD OF THE INVENTION

The present invention relates generally to recombinant viral constructs expressing a protective antigen together with a cytokine and to vaccine compositions comprising same. In particular, the present invention is directed to a recombinant viral construct capable of inducing an immune response to an HIV antigen and, most particularly an HIV-1 antigen. The present invention is useful, inter alia, in the therapeutic and/or prophylactic treatment of HIV.

BACKGROUND OF THE INVENTION

Bibliographic details of the publications numerically referred to in this specification are collected at the end of the description.

There is currently no effective method of treating HIV infection. Current treatment strategies can suppress plasma HIV-1 RNA levels to very low levels, however latently infected cells harbouring HIV-1 DNA remain detectable and viral resistance and relapse is common [1,2]. Treatment-induced reductions in HIV-1 levels results in a loss of antigenic stimulus for effective immune responses. HIV-specific cytotoxic T lymphocyte (CTL) responses, thought to be a critical effector mechanism in the control of HIV-1, decline to low levels following effective anti-HIV therapy [3].

Previous trials of therapeutic HIV-1 vaccines have shown that it is possible to stimulate anti-HIV immune responses in HIV-1 infected individuals, but no clinical benefit has been demonstrated [4-6]. Prior studies have used protein-based HIV-1 vaccines incapable of inducing CTL responses or vaccinated individuals with substantial levels of replicating HIV-1. Even moderate levels of replicating HIV-1 results in a loss of HIV-specific CD4+ T-helper (Th) responses which are required to initiate and sustain an effective CTL response [7].

Additionally, no preventative HIV vaccines currently exist. Although simple recombinant avipox vaccines (without co-expression of cytokines) can induce CTL responses in a proportion of human and non-human primate subjects, the response is often weak, transient, or non-existent. There is a need for more reliable vaccine vectors for the induction of HIV specific CTL and Th responses.

In work leading up to the present invention, the inventors have determined that the magnitude and phenotype of the specific immune response to HIV can be enhanced by vaccination with a recombinant fowl pox virus construct comprising both an HIV gag/pol encoding nucleic acid molecule and a cytokine encoding nucleic acid molecule, in particular, IFN-γ.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The subject specification contains nucleotide sequence information prepared using the programme PatentIn Version 2.0, presented herein after the bibliography. Each nucleotide sequence is identified in the sequence listing by the numeric indicator <210> followed by the sequence identifier (e.g. <210>1, <210>2, etc). The length, type of sequence (DNA, etc) and source organism for each nucleotide sequence are indicated by information provided in the numeric indicator fields <211>, <212> and <213>, respectively. Nucleotide sequences referred to in the specification are defined by the information provided in numeric indicator field <400> followed by the sequence identifier (e.g. <400>1, <400>2, etc).

One aspect of the present invention provides a recombinant viral construct comprising an avipox viral vector or functional derivative thereof which incorporates a first nucleic acid molecule encoding one or more HIV antigens or derivatives thereof and a second nucleic acid molecule encoding a cytokine or functional derivative thereof wherein said recombinant viral construct is effective in inducing, enhancing or otherwise stimulating an immune response to said HIV antigen.

Another aspect of the present invention there is provided a recombinant viral construct comprising an avipox viral vector or functional derivative thereof which incorporates a first nucleic acid molecule encoding one or more HIV-1 antigens or derivatives thereof and a second nucleic acid molecule encoding a cytokine or functional derivative thereof wherein said recombinant viral construct is effective in inducing, enhancing or otherwise stimulating an immune response to said HIV-1 antigen.

Yet another aspect of the present invention provides a recombinant viral construct comprising an avipox viral vector or functional derivative thereof which incorporates a first nucleic acid molecule encoding HIV-1 Gag and/or Pol or derivatives thereof and the second nucleic acid molecule encoding a cytokine or functional derivative thereof wherein said recombinant viral construct is effective in inducing, enhancing or otherwise stimulating an immune response to said Gag and/or Pol.

Still yet another aspect of the present invention provides a recombinant viral construct comprising an avipox viral vector or functional derivative thereof which incorporates a first nucleic acid molecule encoding HIV-1 Gag and/or Pol or derivatives thereof and a second nucleic acid molecule encoding interferon-γ or functional derivative thereof wherein said recombinant viral construct is effective in inducing, enhancing or otherwise stimulating an immune response to said Gag and/or Pol.

A further aspect of the present invention provides a recombinant viral construct, comprising a fowl pox viral vector or functional derivative thereof which incorporates a first nucleic acid molecule encoding HIV-1 Gag and/or Pol or derivatives thereof and a second nucleic acid molecule encoding interferon-γ of functional equivalent thereof wherein said recombinant viral construct is effective in inducing, enhancing or otherwise stimulating an immune response to said Gag and/or Pol.

Another further aspect of the present invention relates to a vaccine comprising a recombinant viral construct which construct comprises a avipox viral vector or functional derivative thereof which incorporates a first nucleic acid molecule encoding one or more HIV-antigens or derivatives thereof and a second nucleic acid molecule encoding a cytokine or functional derivative thereof wherein said recombinant viral construct is effective in inducing, enhancing or otherwise stimulating an immune response to said HIV-antigens.

Still another further aspect of the present invention provides a vaccine comprising a recombinant viral construct which construct comprises an avipox viral vector or functional derivative thereof which incorporates a first nucleic acid molecule encoding HIV-1 Gag and/or Pol or derivatives thereof and a second nucleic acid molecule encoding interferon γ or functional derivative thereof wherein said vaccine is effective in inducing, enhancing or otherwise stimulating an immune response to said Gag and/or Pol.

Still yet another aspect of the present invention provides a pharmaceutical composition for use in inducing, enhancing or otherwise stimulating an immune response to HIV in a mammal comprising a recombinant viral construct as hereinbefore defined and one or more pharmaceutically acceptable carriers and/or diluents. The composition may also comprise the recombinant viral construct together with a known antiviral compound or molecule.

Still yet another further aspect of the present invention provides a method of inducing, enhancing or otherwise stimulating an immune response, in a mammal, to HIV said method comprising administering to said mammal an effective amount of a vaccine as hereinbefore defined, for a time and under conditions sufficient to induce, enhance or otherwise stimulate an immune response to one or more HIV antigens.

Still another aspect of the present invention provides a method of inducing, enhancing or otherwise stimulating an immune response, in a mammal, to HIV said method comprising administering to said mammal an effective amount of a recombinant viral construct as hereinbefore defined for a time and under conditions sufficient to induce, enhance or otherwise stimulate an immune response to one or more HIV antigens.

Yet another aspect of the present invention provides a method of treating a mammal, said method comprising administering to said mammal an effective amount of a vaccine as hereinbefore defined for a time and under conditions sufficient to induce, enhance or otherwise stimulate an immune response to one or more HIV antigens.

Yet another aspect of the present invention provides a method of treating a mammal, said method comprising administering to said mammal an effective amount of a recombinant viral construct as hereinbefore defined for a time and under conditions sufficient to induce, enhance or otherwise stimulate an immune response to one or more HIV antigens.

Yet another aspect of the present invention provides a method for the treatment and/or prophylaxis of HIV infection or AIDS in a mammal, said method comprising administering an effective amount of a vaccine as hereinbefore defined for a time and under conditions sufficient to induce, enhance or otherwise stimulate an immune response to one or more HIV antigens.

Yet another aspect of the present invention provides a method for the treatment and/or prophylaxis of HIV infection or AIDS in a mammal, said method comprising administering an effective amount of a recombinant viral construct as hereinbefore defined for a time and under conditions sufficient to induce, enhance or otherwise stimulate an immune response to one or more HIV antigens.

The present invention further extends to the use of the subject recombinant viral construct in the manufacture of a medicament for the treatment and/or prophylaxis of HIV infection.

Yet another aspect of the present invention provides an agent useful for inducing, enhancing or otherwise stimulating an immune response to HIV said agent comprising a recombinant viral construct as hereinbefore defined.

DETAILED DESCRIPTION OF THE PREFERRED EMBODIMENTS

The present invention is predicated, in part, on the determination that the immune response to HIV, and in particular HIV-1, can be enhanced when vaccination is performed utilising a recombinant viral construct comprising both a nucleic acid molecule encoding one or more protective HIV antigens, such as gag/pol, and a nucleic acid molecule encoding a cytokine, such as IFN-γ.

Accordingly, one aspect of the present invention provides a recombinant viral construct comprising an avipox viral vector or functional derivative thereof which incorporates a first nucleic acid molecule encoding one or more HIV antigens or derivatives thereof and a second nucleic acid molecule encoding a cytokine or functional derivative thereof wherein said recombinant viral construct is effective in inducing, enhancing or otherwise stimulating an immune response to said HIV antigen.

Reference herein to "HIV" should be understood as including reference to any HIV strain including homologues and mutants. In a particularly preferred embodiment said HIV is HIV-1.

According to this preferred aspect of the present invention there is provided a recombinant viral construct comprising an avipox viral vector or functional derivative thereof which incorporates a first nucleic acid molecule encoding one or more HIV-1 antigens or derivatives thereof and a second nucleic acid molecule encoding a cytokine or functional derivative thereof wherein said recombinant viral construct is effective in inducing, enhancing or otherwise stimulating an immune response to said HIV-1 antigen.

Reference to "inducing, enhancing or otherwise stimulating" an immune response to an HIV-1 antigen should be understood as stimulating or facilitating the stimulation of a specific immune response. The specific immune response may be a T-cell and/or humoral response which is directed to any one or more peptides or epitopes, respectively, of the HIV antigen encoded by the nucleotide sequence comprising the recombinant viral construct of the present invention. Preferably, the immune response is a Th-1 and CTL response. However, even where an immune response is skewed to a Th-1 type response, some degree of antibody generation may nevertheless occur.

Reference to "HIV antigen or derivative thereof" should be understood as a reference to any component of HIV or derivative thereof. Said component may be a peptide, polypeptide, protein or non-proteinaceous fragment such as a carbohydrate. It should be understood that the antigen may comprise one or more sites in respect of which a specific immune response is stimulated. For example, processing of the antigen by an antigen presenting cell may result in the production of one or more peptides which are co-expressed with MHC class II and which stimulate specific T helper cells. Similarly, the processing and co-expression of said peptides together with MHC class I may lead to the stimulation of one or more specificities of T cytotoxic cells. Said antigen may also comprise one or more epitopes to which a humoral immune response may be directed. Said epitope may be a linear or a conformational epitope. Where the epitope is a linear epitope, folding of the expressed antigen into its native conformation may not be required to achieve the stimulation of a specific humoral response directed to that epitope. Said antigen may for example comprise only one epitope and may take the form of a hapten. However its co-expression with a cytokine, in accordance with the present invention, may be sufficient to render said hapten immunogenic and therefore suitable for use in the present invention.

Accordingly, it should be understood that reference to stimulating a response to an HIV "antigen" should be understood as a reference to the stimulation of specific immune cells (i.e. T cells and/or B cells) which are directed to one or more sites of the HIV antigen. Examples of antigens suitable for use in the present invention include, but are not limited to, one or more of the molecules encoded by the HIV viral genes gag, pro, pol and env. The expression product of each gene is given the same name, but in normal type with the first letter capitalized. Preferably said HIV antigens are the HIV-1 Gag and/or Pol molecules or derivatives thereof.

According to this preferred embodiment there is provided a recombinant viral construct comprising an avipox viral vector or functional derivative thereof which incorporates a first nucleic acid molecule encoding HIV-1 Gag and/or Pol or derivatives thereof and the second nucleic acid molecule encoding a cytokine or functional derivative thereof wherein said recombinant viral construct is effective in inducing, enhancing or otherwise stimulating an immune response to said Gag and/or Pol.

Reference to "cytokine" is a reference to any cytokine or derivative thereof which is capable of modulating the stimulation of an immune response. For example, said cytokine may induce, up-regulate, enhance or maintain an immune response. Particularly preferred cytokines are those which either support a Th1 response, a CTL response or skew a response towards a Th1 type response, for example, IL-2 and γ-interferon or functional equivalents thereof. Preferable said cytokine is γ-interferon.

Accordingly, in a particularly preferred embodiment there is provided a recombinant viral construct comprising an avipox viral vector or functional derivative thereof which incorporates a first nucleic acid molecule encoding HIV-1 Gag and/or Pol or derivatives thereof and a second nucleic acid molecule encoding interferon-γ or functional derivative thereof wherein said recombinant viral construct is effective in inducing, enhancing or otherwise stimulating an immune response to said Gag and/or Pol.

Avipox viral vectors suitable for use in the present invention may comprise the whole or part of any avipox virus or derivative thereof. The present invention should be understood to include derivatives such as modified virus, for example virus which has been attenuated. Examples of avipox viruses suitable for use in the present invention include, but are not limited to, fowl pox virus and canary pox virus. Preferably said avipox virus is fowl pox virus.

In a most preferred embodiment there is provided a recombinant viral construct, comprising a fowl pox viral vector or functional derivative thereof which incorporates a first nucleic acid molecule encoding HIV-1 Gag and/or Pol or derivatives thereof and a second nucleic acid molecule encoding interferon-γ of functional derivative thereof wherein said recombinant viral construct is effective in inducing, enhancing or otherwise stimulating an immune response to said Gag and/or Pol.

Reference to "derivatives" should be understood to include fragments, parts, portions, equivalents, analogs, mutants, homologs, mimetics from natural, synthetic or recombinant sources including fusion proteins. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence. Substitutional amino acid variants are those in which at least one residue in the sequence has been removed and a different residue inserted in its place. Additions to amino acid sequences including fusions with other peptides, polypeptides or proteins.

The derivatives include fragments having particular epitopes or parts of the entire protein fused to peptides, polypeptides or other proteinaceous or non-proteinaceous molecules. For example, the vector or derivative thereof may be fused to a molecule to facilitate its entry into a cell. Derivatives of nucleic acid sequences may be derived from single or multiple nucleotide substitutions, deletions and/or additions including fusion with other nucleic acid molecules. The derivatives of the nucleic acid molecules of the present invention include oligonucleotides, PCR primers, antisense molecules and fusion of nucleic acid molecules.

Equivalents should be understood to include reference to molecules which can act as a functional analog or agonist. Equivalents may not necessarily be derived from the subject molecule but may share certain conformational similarities. Alternatively, equivalents may be designed to mimic certain immunological and physiochemical properties of the subject molecule. Equivalents may be detected following, for example, natural product screening. Equivalents also include peptide mimics. Homologs contemplated herein include, but are not limited to, molecules derived from different species. Fragments include portions which are effective in achieving the object of the present invention.

The nucleic acid molecule suitable for use in the present invention may be DNA or RNA. Preferably said nucleic acid molecule is DNA. Reference to the cytokine or HIV antigen encoded by a nucleic acid molecule is a reference to the expression product of said nucleic acid molecule.

Without limiting the present invention to any one theory or mode of action, it is thought that administration of the recombinant construct of the present invention enhances the phenotype and magnitude of the HIV specific T-cell response. It may also result in expansion of the T-cell repertoire directed to the T-cell antigen comprising the construct of the present invention. A protective immune response against HIV-1 (specifically against the HIV-1 antigen comprising the construct) is therefore stimulated in individuals administered the recombinant viral construct of the present invention.

Administration of the subject viral construct in the form of a pharmaceutical composition, may be performed by any convenient means. The viral construct or agent of the pharmaceutical composition are contemplated to exhibit therapeutic activity when administered in an amount which depends on the particular case. The variation depends, for example, on the human or animal. A broad range of doses may be applicable. Considering a patient, for example, from about 0.1 µg to about 1 mg of construct may be administered per kilogram of body weight per day. Dosage regimes may be adjusted to provide the optimum therapeutic response. For example, several divided doses may be administered daily, weekly, monthly or other suitable time intervals or the dose may be proportionally reduced as indicated by the exigencies of the situation. The construct may be administered in any convenient manner such as by the oral, intravenous (where water soluble), intranasal, intraperitoneal, intramuscular, subcutaneous, intradermal or suppository routes or implanting (e.g. using slow release molecules).

Accordingly, another aspect of the present invention relates to a vaccine comprising a recombinant viral construct which construct comprises a avipox viral vector or functional derivative thereof which incorporates a first nucleic acid molecule encoding one or more HIV-antigens or derivatives thereof and a second nucleic acid molecule encoding a cytokine or functional derivative thereof wherein said recombinant viral construct is effective in inducing, enhancing or otherwise stimulating an immune response to said HIV-antigens.

Preferably said HIV-antigens are HIV-1 Gag and/or Pol. Even more preferably said cytokine is interferon-γ.

According to this preferred embodiment there is provided a vaccine comprising a recombinant viral construct which construct comprises an avipox viral vector or functional derivative thereof which incorporates a first nucleic acid molecule encoding HIV-1 Gag and/or Pol or derivatives thereof and a second nucleic acid molecule encoding interferon γ or functional derivative thereof wherein said vaccine is effective in inducing, enhancing or otherwise stimulating an immune response to said Gag and/or Pol.

Most preferably said avipox viral vector is a fowl pox viral vector.

Yet another aspect of the present invention provides a pharmaceutical composition for use in inducing, enhancing or otherwise stimulating an immune response to HIV in a mammal comprising a recombinant viral construct as hereinbefore defined and one or more pharmaceutically acceptable carriers and/or diluents. The composition may also comprise the recombinant viral construct together with a known antiviral compound or molecule.

The pharmaceutical forms suitable for injectable use include sterile aqueous solutions (where water soluble) and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as licithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 µg and 2000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 µg to about 2000 mg. Expressed in proportions, the active compound is generally present in from about 0.5 µg to about 2000 mg/ml of carrier. In the case of compositions containing supplementary active ingredients, the dosages are determined by reference to the usual dose and manner of administration of the said ingredients.

Still another aspect of the present invention provides a method of inducing, enhancing or otherwise stimulating an immune response, in a mammal, to HIV said method comprising administering to said mammal an effective amount of a vaccine as hereinbefore defined for a time and under conditions sufficient to induce, enhance or otherwise stimulate an immune response to one or more HIV antigens.

Preferably, said HIV is HIV-1.

Still another aspect of the present invention provides a method of inducing, enhancing or otherwise stimulating an immune response, in a mammal, to HIV said method comprising administering to said mammal an effective amount of a recombinant viral construct as hereinbefore defined for a time and under conditions sufficient to induce, enhance or otherwise stimulate an immune response to one or more HIV antigens.

Preferably, said HIV is HIV-1.

Yet another aspect of the present invention provides a method of treating a mammal, said method comprising administering to said mammal an effective amount of a vaccine as hereinbefore defined for a time and under conditions sufficient to induce, enhance or otherwise stimulate an immune response to one or more HIV antigens.

Preferably said HIV antigens are HIV-1 antigens.

Yet another aspect of the present invention provides a method of treating a mammal, said method comprising administering to said mammal an effective amount of a recombinant viral construct as hereinbefore defined for a time and under conditions sufficient to induce, enhance or otherwise stimulate an immune response to one or more HIV antigens.

Preferably said HIV antigens are HIV-1 antigens.

Reference to "mammal" should be understood to include all mammals including primates (e.g. humans, monkeys), livestock animals (e.g. sheep, cows, horses, donkeys, goats, pigs), laboratory test animals (e.g. rats, guinea pigs, rabbits, hamsters), companion animals (e.g. dogs, cats), and captive wild animals (e.g. kangaroos, deer, foxes). Preferably, said animal is a primate and even more preferably a human.

The method of the present invention is useful in the treatment and/or prophylaxis of HIV infection and AIDS. For example, the vaccine of the present invention may be administered into subjects known to be infected with HIV in order induce an immune response against HIV thereby preventing the onset of AIDS. Alternatively, the method of the present invention may be used to reduce serum viral load, to alleviate AIDS symptoms or to induce immunity in mammals thought to be at risk of HIV infection.

The method of the present invention may be particularly useful either early in HIV infection to prevent the establishment of a viral reservoir or for a period after exposure to a possible source of HIV infection.

Yet another aspect of the present invention provides a method for the treatment and/or prophylaxis of HIV infection or AIDS in a mammal, said method comprising administering an effective amount of a vaccine as hereinbefore defined for a time and under conditions sufficient to induce, enhance or otherwise stimulate an immune response to one or more HIV antigens.

Preferably said HIV antigens are HIV-1 antigens.

Still yet another aspect of the present invention provides a method for the treatment and/or prophylaxis of HIV infection or AIDS in a mammal, said method comprising administering an effective amount of a recombinant viral construct as hereinbefore defined for a time and under conditions sufficient to induce, enhance or otherwise stimulate an immune response to one or more HIV antigens.

Preferably said HIV antigens are HIV-1 antigens.

An "effective amount" means an amount necessary at least partly to attain the desired immune response, or to prevent or to delay the onset or inhibit progression or halt altogether, the onset or progression of a particular condition being treated. This amount varies depending upon the health and physical condition of the individual to be treated, the taxonomic group of individual to be treated, the capacity of the individual's immune system to synthesise antibodies, the degree of protection desired, the formulation of the vaccine, the assessment of the medical situation, and other relevant factors. It is expected that the amount will fall in a relatively broad range that can be determined through routine trials.

Reference herein to "treatment" and "prophylaxis" is to be considered in its broadest context. The term "treatment" does not necessarily imply that a mammal is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity of onset of a particular condition. "Treatment" may also reduce the severity of an existing condition or the frequency of acute attacks.

In accordance with this method, the vaccine of the present invention may be co-administered with a known anti-viral compound or molecule. Such compounds or molecules include, but are not limited to, reverse transcriptase inhibitors (for example, Zidovudine or 3TC) or protease inhibitors (for example, Indinavir). By "co-administered" is meant simultaneous administration in the same formulation or in two different formulations via the same or different routes or sequential administration by the same or different routes. By "sequential" administration is meant a time difference of from seconds, minutes, hours or days between the administration of the vaccine and the known anti-viral compound or molecule. The vaccine and the known anti-viral compound or molecule may be administered in any order.

Routes of administration include but are not limited to intravenously, intraperitoneally, subcutaneously, intracranially, intradermally, intramuscularly, intraocularly, intrathecally, intracerebrally, intranasally, infusion via i.v., drip, and implant. Intramuscular routes are particularly preferred.

The present invention further extends to the use of the subject recombinant viral construct in the manufacture of a medicament for the treatment and/or prophylaxis of HIV infection.

Preferably said HIV infection is HIV-1 infection.

Yet another aspect of the present invention provides an agent useful for inducing, enhancing or otherwise stimulating in a mammal, an immune response to HIV said agent comprising a recombinant viral construct as hereinbefore defined.

Further features of the present invention are more fully described in the following non-limiting Examples. It is to be understood, however, that the detailed description is included solely for the purpose of exemplifying the present invention.

EXAMPLE 1

Animals

Macaques (*M. nemestrina*, aged 24-32 months) were free from SRV infection and anaesthetised with Ketamine (10 mg/kg IM) prior to procedures. The studies were approved by the institutional Animal Experimentation and Ethics Committees.

Seven animals were studied that have been previously described [9,10]. Four animals (M2, M3, M4, M5) served as controls and received no vaccines during the course of this study. These 4 animals (M2-5) had been vaccinated with DNA and FPV HIV-1 vaccines (not containing cytokines) 11-19 months prior to study and resisted a HIV-1 challenge 9 months prior to this study. Three animals (M7, M9, M10) had no previous HIV-1 vaccinations and were infected with HIV-1 following an intravenous challenge with HIV-1$_{LA1}$ 9 months prior to this study. Two of these animals (M9, M10) received a novel FPV encoding both gag/pol and human IFNγ and one animal (M7) received a FPV vaccine encoding gag/pol only. Each FPV vaccine was given IM into the anterior thigh at $10^8$ PFU in 0.3 ml twice, 3 months apart at 9 and 12 months following HIV-1 infection.

All macaques were previously vaccinated with 3 doses of tetanus toxoid (CSL, Parkville, Australia) IM prior to HIV-1 vaccinations. Each animal was assessed twice daily, following vaccination, for visible swelling or redness at the site of injection and for activity by counting a variety of normal macaque behaviours (individual and conspecific play, foraging, displacement, mounting and grooming activities) as previously described [11]. A 25% reduction in total activity compared to the mean baseline activity in the week prior to vaccination was considered significant. Daily temperature recordings were determined by using an electronic hand held thermometer (Braun Thermoscan) and training the animals to have this applied to their tongues for $\geq 1$ second. This method of taking temperatures was found to be 0-0.8° C. (mean 0.3° C.) lower than rectal temperatures taken on sedated macaques using a rectal thermometer on 22 consecutive occasions.

EXAMPLE 2

Vaccines

The HIV-1 gag/pol genes with or without the human IFNγ gene have been inserted into the FPV genome, along with the *E. coli* lacZ and gpt marker genes, between the FPV thymidine kinase (TK) region and the 3' open reading frame (ORF). See FIGS. 1 and 2.

Plasmid Constructs

A. Plasmids for Construction of FPV-gag/pol-IFNγ

Figure 1A:
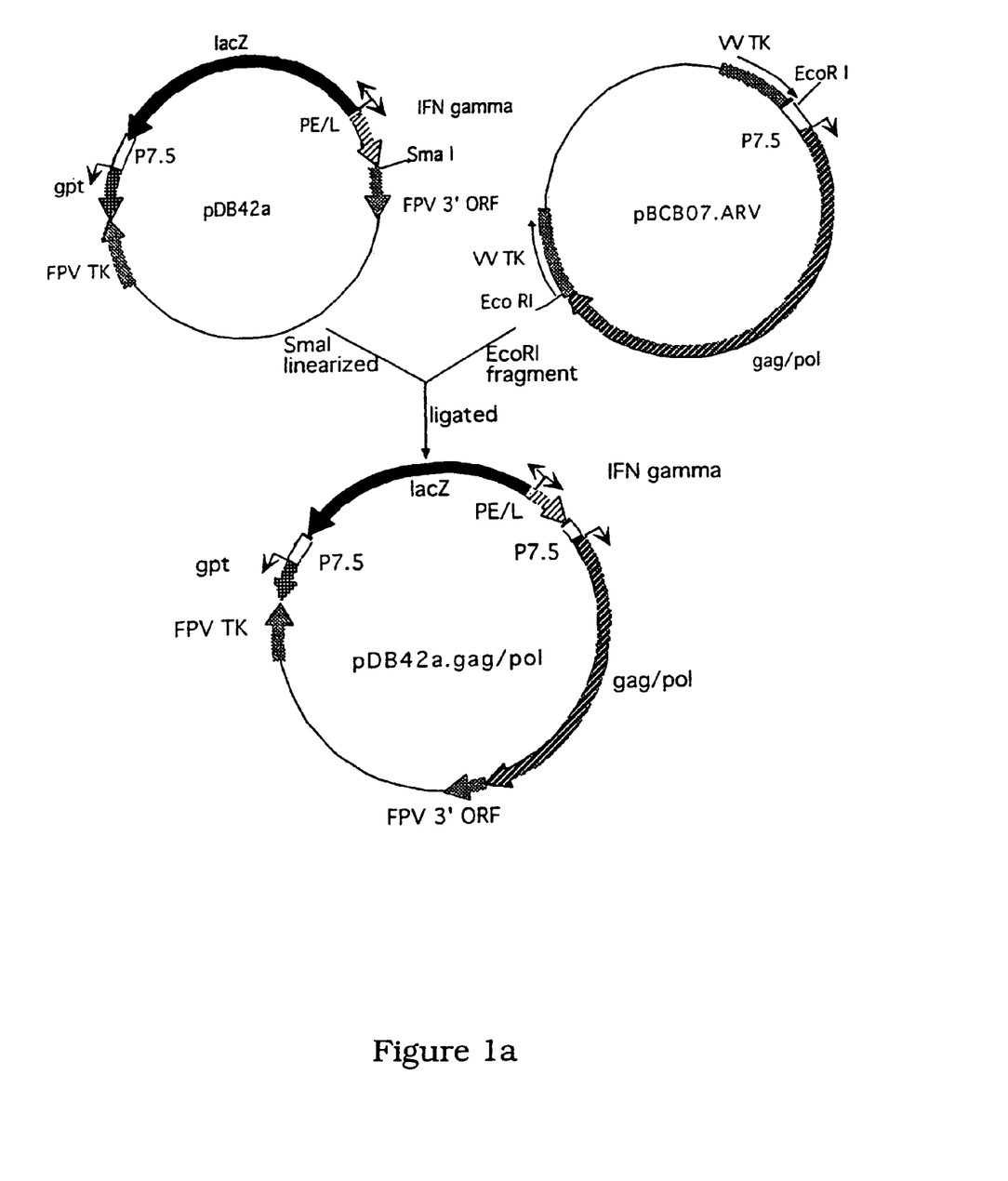
FIG. 1 is a schematic representation of the construction of FPVgag/pol-IFNγ.
Figure 1B:
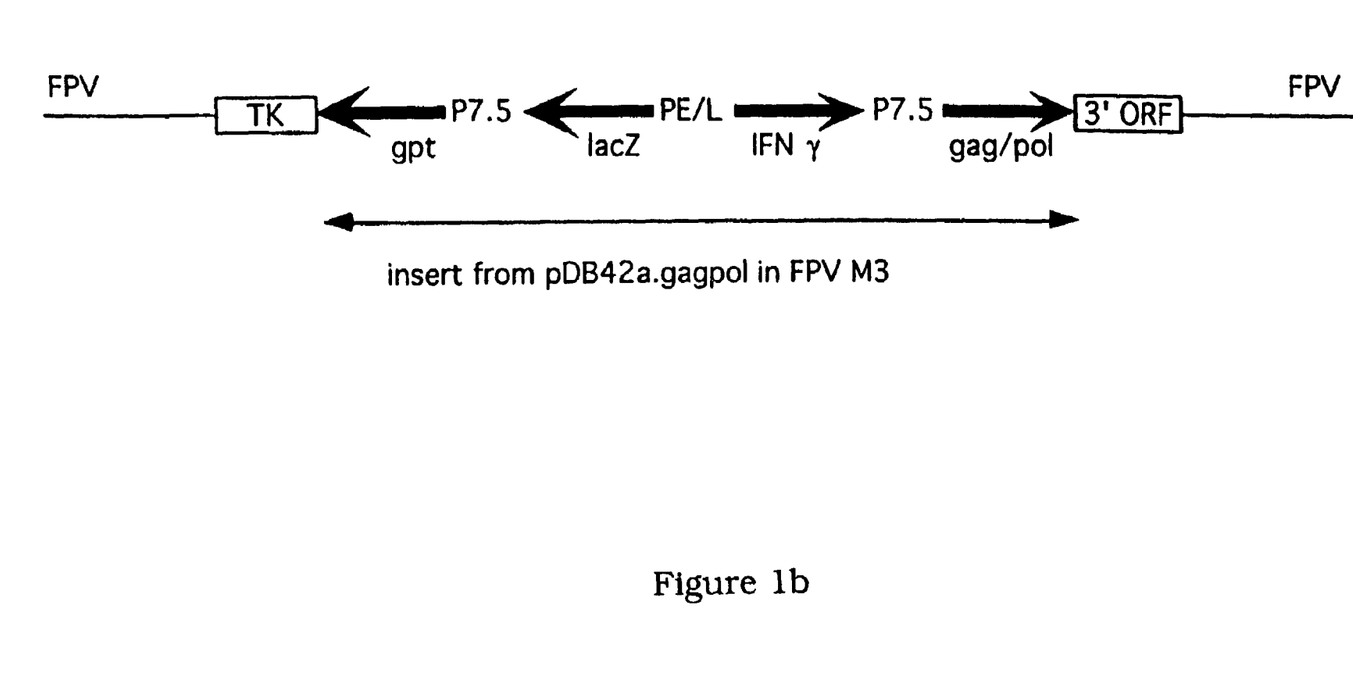

Construction of these plasmids is shown in FIG. 1.

1. The gag/pol genes of HIV-1, isolate ARV-2/SF2, were excised from pUC19.ARV (Chiron Corporation, Emeryville, Calif.) with SacI and NdeI restriction endonucleases. This fragment (corresponding to nucleotides 684-5132, Genbank Accession No. K02007) was blunt-ended with T4 DNA polymerase and inserted into HincII linearized pBCB07 (12) under the control of the vaccinia P7.5 promoter. This plasmid was names pBC07.ARV.

2. The human IFNγ gene coding sequence was derived by PCR from plasmid pUC9-2 template. pUC9-2 contains the 844 bp Sau3A fragment of human IFNγ cDNA (13). The sense PCR primer was 5'-gcttaattctctcgggatcgatg (<400>1). This spans nucleotides 89-111 of the IFNγ cDNA (Genbank Accession No. X13274) with two mismatches introduce to generate a San3A site (bold text). The IFNγ cDNA start codon is underlined. The antisense primer was 5'-attcggatccattacaaaaaaagttgc (<400>2). This spans nucleotides 751-726 of the gene (the antisense strand, downstream of the stop codon at nucleotide 607) with 4 mismatches introduced to generate a BamHI/Sau A site (bold text) and 1 mismatch to generate a TTTTTNT transcription terminator on the sense strand (underlined).

The PCR product was digested with Sau3A and cloned into the BamHI site of pAF09 (14). This places the human IFNγ gene under the control of the FPV P.E/L bidirectional promoter, with the start codon of the gene in frame with the P.E/L start codon. The plasmid was named pDB42a, and also contains the *E. coli* lacZ and gpt marker genes, under the control of the P.E/L and vaccinia P.7.5 promoters, respectively, and the fowlpox TK gene and 3'ORF regions to facilitate recombination.

3. The gag/pol genes and P7.5 promoter were excised from pBC07.ARV by EcoRI digestion, blunted with T4 polymerase, and cloned into SmaI linearized pDB42a. This plasmid, pDB42a.gag/pol, was used for construction of FPV-gag/pol-h IFNγ.

B. Plasmids for Construction of FPV-gag/pol

Figure 2A:
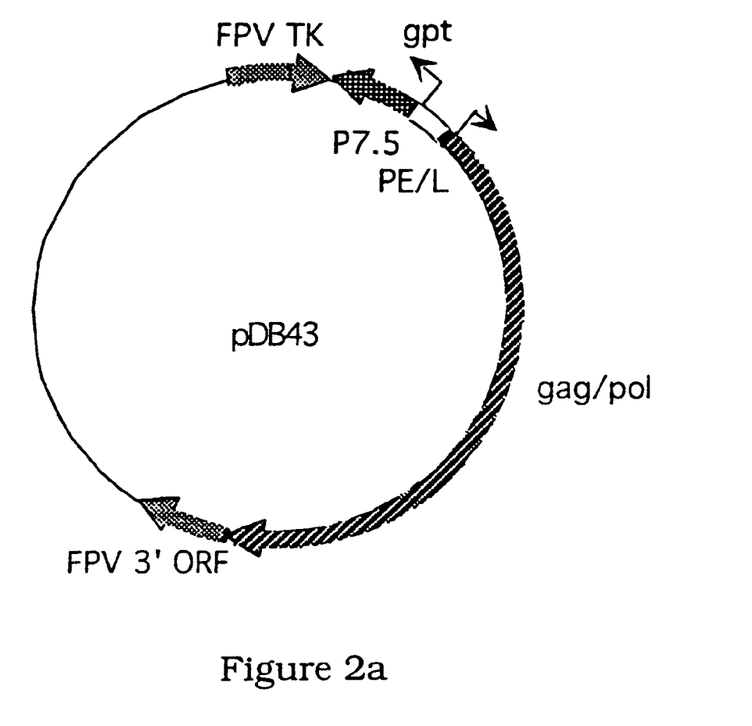
FIG. 2 is a schematic representation of the construction of FPVgag/pol.
Figure 2B:
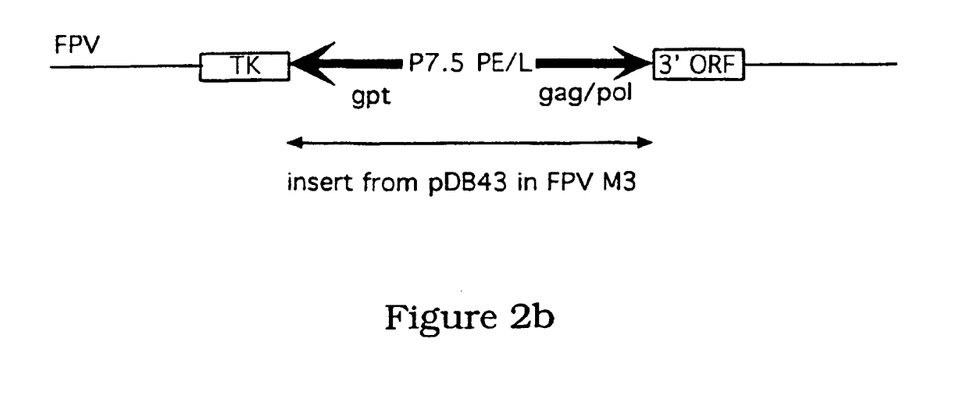

Construction of these plasmids is shown in FIG. 2.

1. The gag/pol genes in HIV-1 were derived by PCR with pUC19.ARV (see 1 above) as template. The sense PCR primer was 5'-taattatcgataataaatgggtgcgagagcg (<400>3). This contains sequence from the P.E/L promoter and nucleotides 791-805 of the HIV-1 gag/pol gene (Genbank Accession No. K02007). The start codon of the gag gene product is underlined the bold text indicates a ClaI site. The antisense primer was 5'-aaaggatcctttagcmctttaaaaaaaaacatatgg (<400>4). This spans nucleotides 5164-5128 of the gene (on the antisense strand, downstream of the pol stop codon at nucleotide 5101). Two mismatches were introduced to generate a BamHI site (bold text) and 4 mismatches to generate 2 overlapping TTTTTNT transcription terminators on the sense strand (underlined).

The PCR product was digested with ClaI and BamHI and cloned between the ClaI and BamHI sites of pAF04 (D. Boyle, personal communication). This places the gag/pol genes under the control of the FPV P.E/L bidirectional promoter, aligned so that the native start codon of the gag gene is utilised. This is essential for expression and myristilation of the gag gene product. The plasmid was named pDB43, and also contains the E. coli gpt marker gene, under the control of the vaccinia P7.5 promoter, and the FPV TK tgene and 3'ORF regions to facilitate recombination.

Virus Construction

Recombinant viruses were constructed by standard methods (15), by transfecting FPV-M3 infected chick cells with pDB42a.gag/pol or pDB43. Homologous recombination between both the tgene and the 3' ORF regions of the plasmids and the wild type virus results in insertion of HIV gag/pol and gpt genes (with and without the h IPNγ and lacZ genes) into the virus. The gpt gene confers resistance to mycophenolic acid, recombinant viruses were amplified and selected after several rounds of plaque purification in the presence of mycophenolic acid. PCR with primers complementary to sequences flanking the insertion site was used to confirm the absence of wild-type parent virus.

EXAMPLE 3

Blood Cell Counts and Plasma Biochemistry

To determine whether the vaccine-expressed IFNγ resulted in abnormalities in plasma biochemistry or blood cell counts, a battery of biochemical and cellular analyses were performed on serial blood samples from the macaques. Multiparameter biochemical analyses and blood counts were performed on automated machines and counts confirmed manually. White cell counts and differential were confirmed by manual counting. PBMC obtained before and after vaccinations were stained for monocyte and T cell markers and analysed by flow cytometry as previously described [9] using antibodies directed against CD2 (Leu5-PE, Becton Dickinson, San Jose, Calif.), CD4 (OKT4-FITC, Ortho Diagnostics, Raritan, N.J.), CD8 (Leu2a-FITC, Becton Dickinson), and CD14.

EXAMPLE 4

HIV-1 Antibody and Th Responses

Plasma was assessed for HIV-1 antibodies by particle agglutination (Serodia-HIV, Fujirebio, Japan) and Western blotting using 200 µg of standard mixed HIV-1 protein stock [9]. Lymphoproliferative responses were assessed by standard $^3$-H-thymidine incorporation assay as described [9]. Macaque PBMC in triplicate wells at $10^5$ cells/well were stimulated for 6 d with 10 µg/ml of recombinant HIV-1$_{SF2}$ gp120 or HIV-1$_{SF2}$p24 (Chiron) in media containing 10% autologous heat-inactivated serum and pulsed with $^3$H-thymidine before β-counting. PBMC were also incubated with media alone or media supplemented with 10 µg/ml culture derived control antigens to assess unstimulated control responses, and stimulated with PHA (10 µg/ml) or tetanus toxoid antigen (0.01 Lf/ml) as positive mitogenic and antigenic control responses. Proliferation is expressed as stimulation index (SI, mean $^3$H-thymidine incorporation of cells stimulated with antigen/mean incorporation in absence of antigenic stimulation). Supernatants from selected lymphoproliferative cultures were assayed for the presence of IL-4 and IFNγ by EIA (Genzyme, Cambridge, Mass.).

EXAMPLE 5

Quantitative HIV-Specific CTL Analyses

Analysis of CTL precursor frequencies to HIV-1 Env and Gag/Pol antigens in macaque PBMC of macaques was performed by a limiting dilution analysis [9]. PBMC were plated in 96 well round-bottomed plates in 7 serial 1.5-fold dilutions of $10^5$ to 8.8-$10^3$ cells/well in 24 replicates. Each well was stimulated with $10^4$ autologous PBMC infected with a recombinant vaccinia virus expressing HIV-1$_{LA1}$Env/Gag/Pol antigens and supplemented with 10 U/ml rIL-2 (Hoffman-La Roche, Nutley, N.J.) every 3-4 d. After 10-14 d, cells in each well were assayed for cytolytic activity against autologous target cells infected with wild type vaccinia or recombinant vaccinia expressing HIV-1$_{LA1}$Env antigens or HIV-1$_{LA1}$Gag/Pol. Wells were considered positive if cytolysis exceeded the mean spontaneous release from that target by 3 SD. CTL frequencies and 95% confidence intervals were determined by maximum likelihood analysis with software provided by S Kalams, Harvard Medical School [16]. Target cells were autologous B lymphoblastoid cell lines (BLCL), established from each macaque by infecting PBMC with H. papio, a baboon herpresvirus [9]. BLCL could not be transformed with PBMC of one control animal (M4) and could not be maintained in long term culture from one vaccinated animal (M10) and CTL data could not be generated from those animals.

EXAMPLE 6

Analysis of HIV-1 DNA and Viral Levels

HIV-1 gag and HLA-DQ DNA were amplified from extracted DNA form PBMC samples and quantified using primer pairs SK38/39 and GH26/27 (Gibco-BRL) respectively using PCR conditions as described [9]. DNA from $10^5$ PBMC was standardised according to the DQ band density in comparison to 8E5 cell DNA (which contains 1 HIV-1 DNA copy/cell) and confirmed by measuring absorbance on a spectrophotometer (Ultrospec 3000, Pharmacia Biotech) at 260 mm. Virus isolation was performed by cocultivating $10^6$ macaque PBMC with 106 PHA-stimulated pooled human PBMCs and 50 U/ml IL-2. Fresh media and IL-2 were added to the cultures twice weekly and PHA-stimulated human PBMC added weekly for 4 weeks. HIV-1 was quantified in cultures supernatants by HIV-1 p24 EIA (Abbott Laboratories, Abbott Park, Ill.).

EXAMPLE 7

Safety of FPV Expressing IFNγ

Figure 3A:
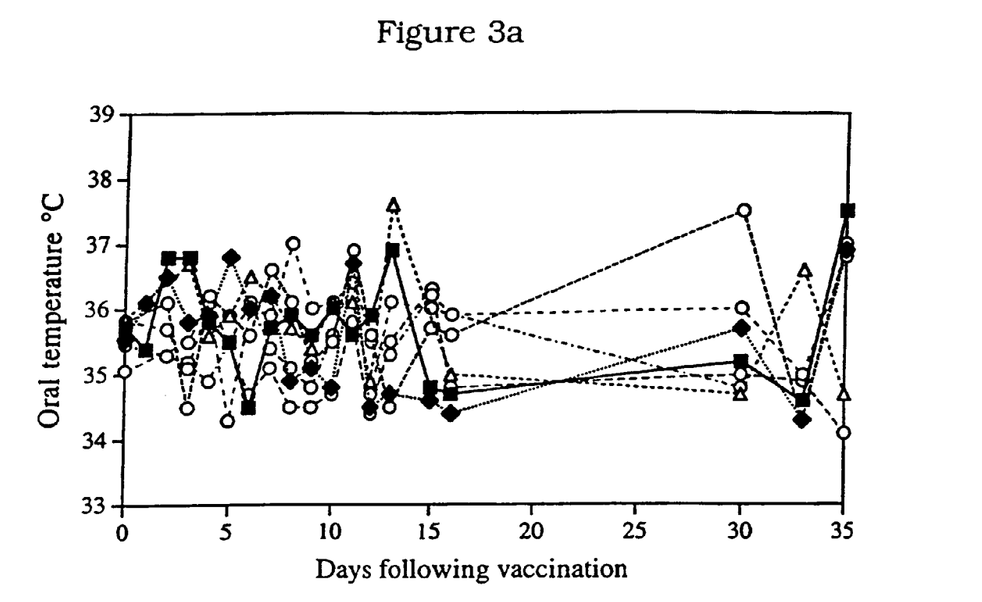
FIG. 3 is a graphical representation of the safety of FPVgag/pol-IFNγ immunisation. A. No significant fever was documented following FPVgag/pol-IFNγ vaccination of macaques. Animals M9 and M10 (♦,■) received FPVgag/pol-IFNγ $10^8$ PFU IM, animal M7 (Δ) received FPVgag/pol, and animals M2, M3, M4 and M5 (○) were unvaccinated controls. B. No change in T cell or monocyte counts was observed following FPVgag/pol-IFNγ vaccination of macaques. PBMC obtained from animals vaccinated with FPVgag/pol-IFNγ (M9, M10) or FPVgag/pol (M7) were stained for $CD4^+$ T cells, $CD8^+$ T cells and $CD14^+$ monocytes prior to vaccination (Δ, 6 times over 8 months prior to vaccination, mean±SD shown) on the day of vaccination (○) and following vaccination (■, weekly for 4 weeks following vaccination, mean±SD shown).
Figure 3B:
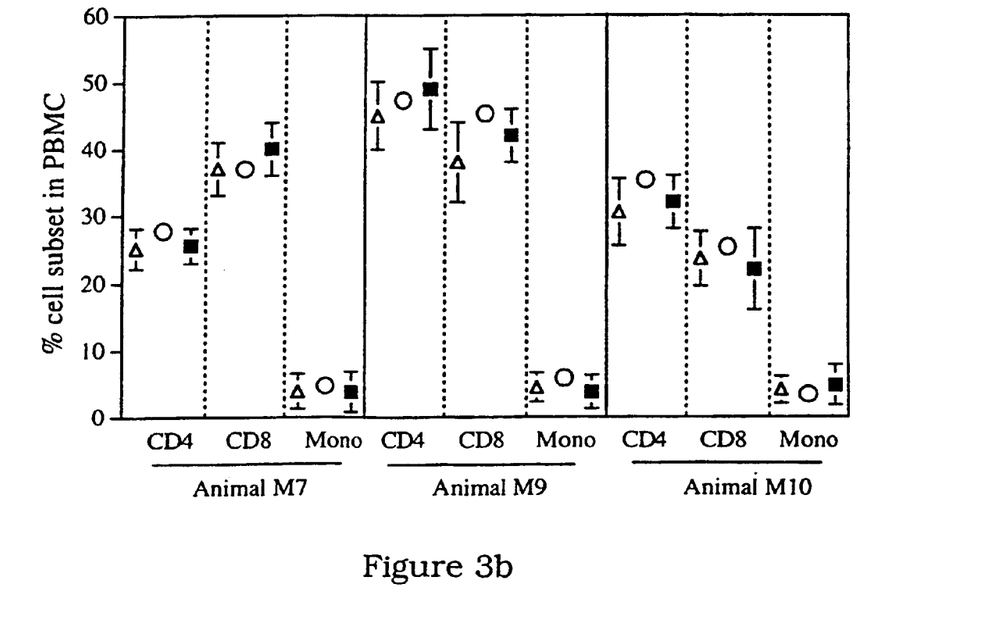

Locally delivered cytokines encoded by viral vectors are generally less toxic than systemically administered cytokines [8]. We analysed the reactogenicity of FPVgag/pol-IFN-γ in comparison to 4 matched controls not immunized and a control animal receiving FPVgag/pol-IFNγ only. A high dose of the FPV vaccines was administered ($10^8$ FPU) in an attempt to detect any significant adverse effects. A 44-75% reduction in activity of all 3 FPV-immunised macaques was observed for the first 24 hrs following vaccination, and in one of two FPVgag/pol-IFNγ immunised animal (M9), 28% reduction of activity was present between 24 to 48 hrs, but was normal thereafter in all animals. Swelling at the injection site was observed for 1-2 days following vaccinations in all 3 FPV vaccinated animals. No fever was documented following the FPV vaccinations (FIG. 3a). All animals gained weight normally. No change in $CD4^+$ or $CD8^+$ T cell subsets, or monocyte levels in PBMC were observed following vaccination by (FIG. 3b). Additionally, no significant changes in plasma electrolytes, renal function as assessed by plasma creatinine and urea, liver function markers, haemoglobin, white cell counts or platelet counts were observed following FPVgag/pol or FPVgag/pol-IFNγ vaccination.

EXAMPLE 8

T Cell Immunogenicity

Figure 4A:
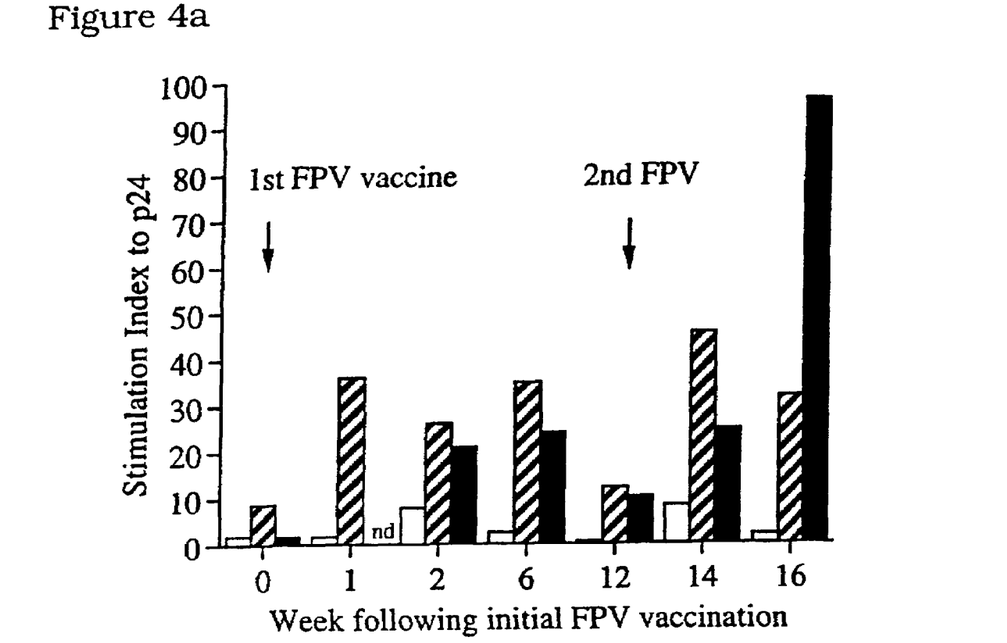
FIG. 4 is a graphical representation of enhanced gag-specific Th1 response following FPVgag/pol-IFNγ vaccination of macaques. A. T cell proliferative response to p24 antigen was measured serially following 2 vaccinations (arrows) of macaques with FPVgag/pol-IFNγ (animals M9, M10, solid and hatched bars) or FPVgag/pol vaccinations of macaques (animal M7, open bars). B. Secretion of IFN-γ and IL-4 by PBMC in response to recombinant HIV-1$_{SF2}$p24 protein stimulation obtained before and after the first FPV vaccination. FPVgag/pol-IFNγ vaccinated macaques (M9 and M10) and a FPVgag/pol immunised animal (M7) is shown.

To determine whether vaccination with FPVgag/pol-IFNγ enhanced Gag/pol specific Th responses, macaques infected with HIV-1 9 months previously were vaccinated twice with FPVgag/pol-IFNγ (2 animals, M9 and M10) or FPVgag/pol (1 animal, M7). Th proliferative response to p24 Gag protein was enhanced 4-7 fold 1-2 weeks after the first FPVgag/pol-IFNγ vaccination and was greater than baseline levels 3 months later (FIG. 4a). Following a second FPVgag/pol-IFNγ vaccination, p24-specific Th responses were further boosted above baseline (5-30 fold) and maintained for at least a further 2 months. The animal which received 2 FPVgag/pol immunisations had a 3 fold enhancement of p24-specific Th response. Tetanus-specific Th responses did not change following FPV vaccinations (<3 fold variation over time). The Th responses to Gag or tetanus antigens of 4 control macaques (M2, M3, M4, M5) did not change, with a <2 fold variation over the 4 month observation period (means SI to p24 was 3.2 and to Tetanus toxoid 3.6).

Figure 4B:
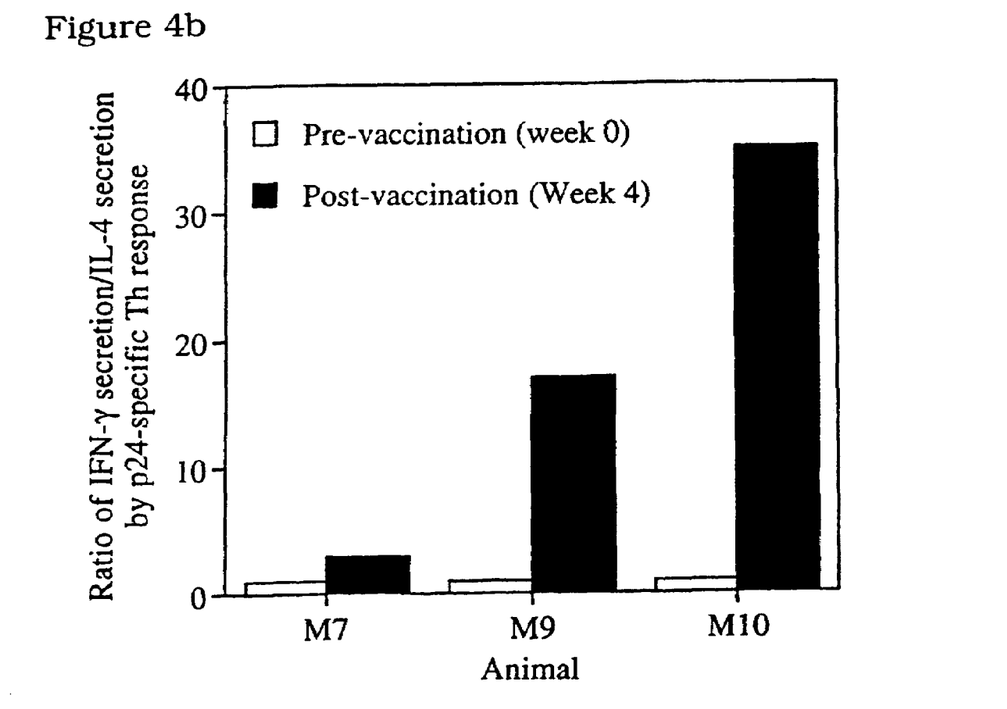

We also assessed whether FPVgag/pol-IFNγ vaccination of HIV-1 infected animals was associated with a change in the phenotype of Gag-specific Th response. Enhanced IFNγ secretion, but not IL-4 secretation, by Gag-specific Th responses from PBMC of animals receiving both FPVgag/pol and FPVgag/pol-IFNγ was observed, with the magnitude of the modulation of the cytokine secretion being greater in the FPVgag/pol-IFNγ immunised animals (FIG. 4b). No change in the tetanus-specific Th phenotype from animals M7, M9 and M10 was observed following FPV vaccinations, with IL-4 secretion exceeding that of IFNγ (by 4-12 fold) both before and 2-6 weeks after FPV vaccinations of all 3 FPV vaccinated animals.

EXAMPLE 9

HIV-Specific CTL Activity Following FPVgag/pol-IFNγ Immunisation

Figure 5:
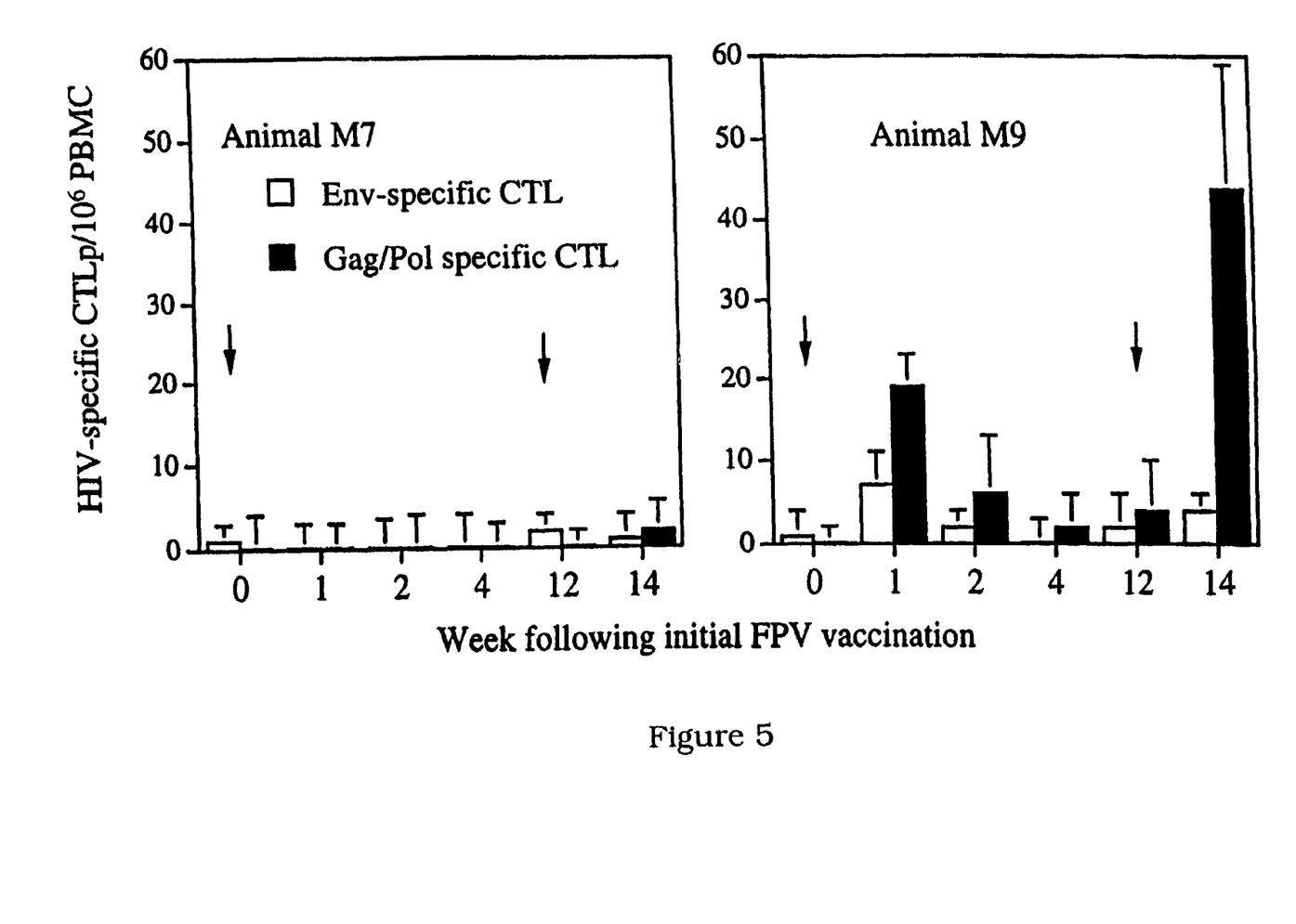
FIG. 5 is a graphical representation of enhanced Gag/pol specific CTL response following FPVgag/pol-IFNγ vaccination. Quantification of CTL precursors to Env and Gag/pol antigens was analysed following FPV vaccinations. CTL frequencies were assessed following initial and booster FPV vaccinations (arrows). Recognition of control targets expressing vaccinia antigens alone have been subtracted.

Considerable interest currently focuses on immunisation strategies to maintain CTL responses in the face of marked reduction in antigenic stimulus from replicating HIV-1 [2, 5]. HIV-1 specific CTL response in macaques parallel the reduction in HIV-1 DNA following the first few months of HIV-1 infection, and in the "latent" phase HIV-1 specific CTL responses are low ($\leq 10$ HIV specific CTLs/$10^6$ PBMC) [9]. By a limiting dilution analysis, CTL precursors to Gag/Pol (but not Env) antigens were enhanced from <5 to $15/10^6$ PBMC following one FPVgag/pol-IFNγ vaccination and to $44/10^6$ PBMC following a second FPVgag/pol-IFNγ vaccination (FIG. 3). Gag/Pol or Env specific CTLs were not detectably enhanced (remaining $\leq 5/10^6$ PBMC) in controls animals either unvaccinated (M2, M3, M5) or vaccinated with FPVgag/pol-IFNγ without IFNγ (M7, FIG. 5).

EXAMPLE 10

HIV-1 Levels Following Vaccination

To determine whether FPVgag/pol-IFNγ vaccination altered HIV-1 viral levels in macaques previously infected with HIV-1, HIV-1 DNA and culturable virus were studied before and after vaccinations. Using env-specific primers, animals M7, M9 and M10 had $\leq 10$ copies of HIV-1 DNA/$10^5$ PBMC 0, 1 and 4 months prior to vaccinations and remained at $\leq 10$ copies of HIV-1 DNA/$10^5$ PBMC at 1, 2 and 4 weeks following the first FPV vaccination, without detectable changes in HIV-1 DNA levels. HIV-1 could not be recovered from cocultured PBMC from any of the 3 vaccinated FPV animals either prior to (weeks 0, −4) or following (weeks +1, +2, +4, +6) vaccination. The cocultured method employed has routinely recovered HIV-1 when plasma HIV-1 RNA levels were 100-400 copies [(9); (10)], suggesting a significant rise in HIV-1 plasma RNA did not occur.

EXAMPLE 11

HIV-1 Antibody Levels

Figure 6:
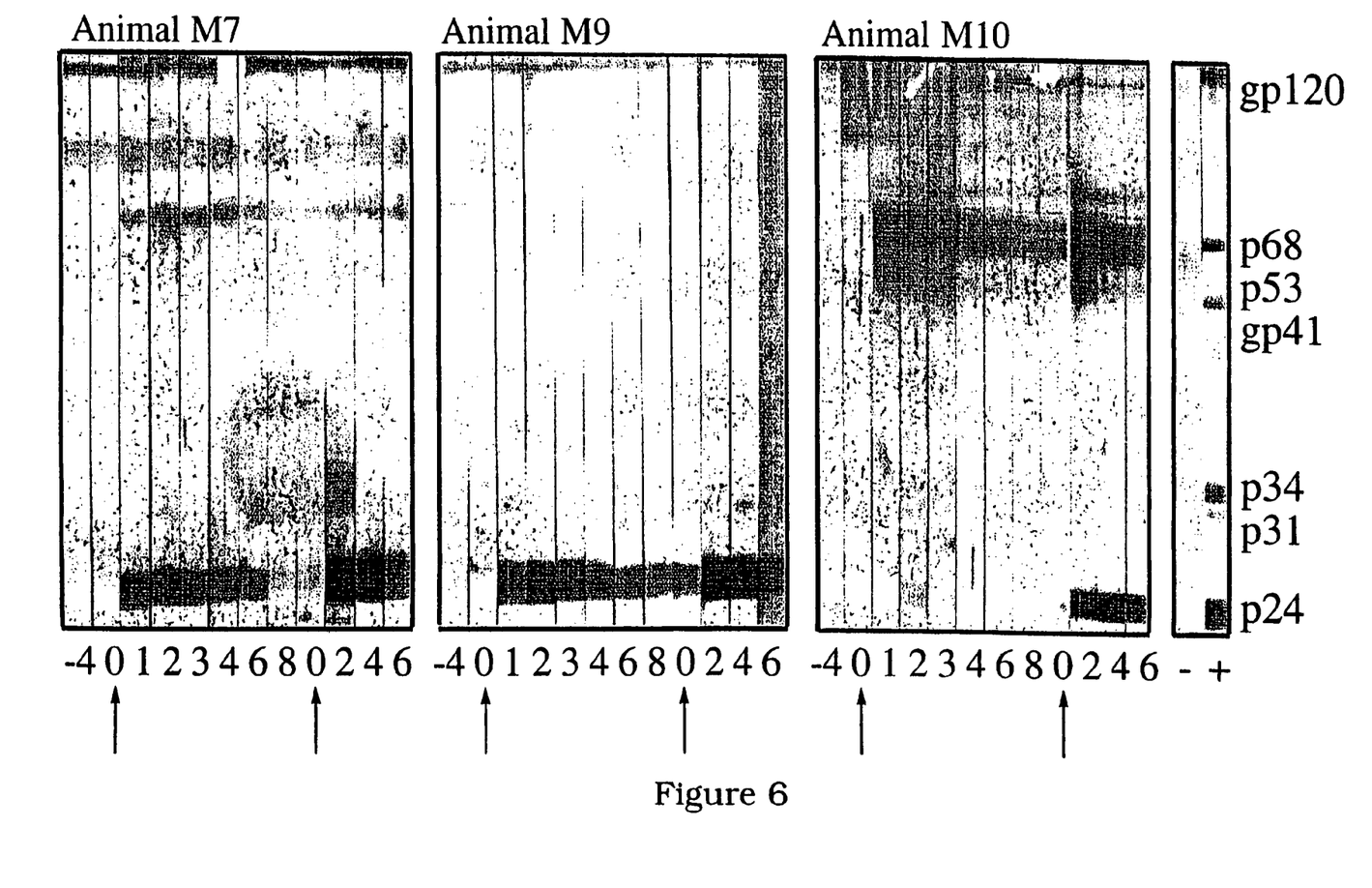
FIG. 6 is a photographic representation of Gag/pol specific antibodies are enhanced following FPVgag/pol vaccination. Western blotting of serial plasma (1:100 dilution) from animals M7, M9 and M10 following FPV vaccinations (arrows). Strips are labelled with weeks prior to or following the first and second vaccinations. Negative and positive controls represent uninfected and HIV-1 infected humans respectively.

Gag/Pol specific antibodies were also enhanced following the 2 FPV vaccinations (FIG. 6). p24-specific antibodies were enhanced in all 3 vaccinated animals, with no difference observed between the FPVgag/pol-IFNγ and FPVgag/pol vaccinated animals. No change in gp120 antibody responses was observed.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

1. Fatkenheuer, G., Thiesen, A., Rockstroh, J., et al. *Aids* (11):F-113-116 (1997).
2. Finzi, D., Hermankova, M., Pierson, T., et al. *Science* 278:1295-1300 (1997).
3. Ogg, G. S., Jin, X., Bonhoeffer, S., et al., *Science* 279:2103-2106 (1998).
4. Tsoukas, C. M., Raboud, J., Bernard, N. F., et al., *AIDS Res Hum Restroviruses* 14:483-490 (1998).
5. Eron, J. J. Jr., Ashby, M. A., Giordano, M. F., et al., *Lancet* 348:1547-1551 (1996).
6. Veenstra, J., Williams, I. G., Colebunders, R., et al., *J Infect Dis* 174:862-866 (1996).
7. Rosenberg, E. S., Billingsley, J. M., Caliendo, A. M., et al., *Science* 2478:1447-1450 (1997).
8. Agy, M. B., Frumkin, L. R., Corey, L., et al. *Science* 257:103-106 (1992).
9. Kent S. J., Woodward, A., Zhao, A. *J Infect Dis* 176:1188-1197 (1997).
10. Kent, S. J., Zhao, A., Best, S., Chandler, J. D., Boyle, D. B., Ramshaw I. A. *J Virol* 72:10180-10188 (1998).
11. Cardinal, B., Kent, S. J., *Lab. Primate Newsletter* (1997).
12. Andrew, M. E., Boyle, D. B., Coupar, B. E., Whitfeld, P. L., Both, G. W., Bellamy, A. R. *J Virol* 61:1054-1060 (1987).
13. Gray, P., Leung, D., Pennica, D., et al., *Nature* 295:503-508 (1982).
14. Heine, H. G., Boyle, D. B. *Arch Virol* 131:277-292 (1993).
15. Boyle, D. B., Coupar, B. E. *Gene* 65:123-128 (1988).
16. de St. Groth, F. *J Immunol Methods* 49:R11-23 (1982).

The invention claimed is:

1. A recombinant viral construct comprising a fowlpox virus vector or functional derivative thereof which incorporates a first nucleic acid molecule encoding HIV Gag and/or Pol or derivatives thereof and a second nucleic acid molecule encoding γ-interferon or functional derivative thereof wherein said recombinant viral construct is effective in inducing, enhancing or otherwise stimulating an immune response to said Gag and/or Pol.

2. A pharmaceutical composition comprising the recombinant viral construct according to claim 1 together with one or more pharmaceutically acceptable carriers and/or diluents.

3. A method of inducing, enhancing or otherwise stimulating, in a mammal, an immune response to HIV said-method comprising administering to said mammal an effective amount of the viral construct according to claim 1 for a time and under conditions sufficient to induce, enhance or otherwise stimulate an immune response to one or more HIV antigens.

4. The method according to claim 3 wherein said HIV is HIV-1.

* * * * *

SEQUENCE LISTING

```
<160> NUMBER OF SEQ ID NOS: 4

<210> SEQ ID NO 1
<211> LENGTH: 23
<212> TYPE: DNA
<213> ORGANISM: mammalian

<400> SEQUENCE: 1
gcttaattct ctcgggatcg atg                                    23

<210> SEQ ID NO 2
<211> LENGTH: 26
<212> TYPE: DNA
<213> ORGANISM: mammalian

<400> SEQUENCE: 2
attcggatcc attacaaaaa agttgc                                 26

<210> SEQ ID NO 3
<211> LENGTH: 31
<212> TYPE: DNA
<213> ORGANISM: mammalian

<400> SEQUENCE: 3
taattatcga taataaatgg gtgcgagagc g                           31

<210> SEQ ID NO 4
<211> LENGTH: 37
<212> TYPE: DNA
<213> ORGANISM: mammalian

<400> SEQUENCE: 4
aaaggatcct ttagctttct taaaaaaaa catatgg                      37
```